United States Patent
Rothman (12)

(10) Patent No.: US 6,207,699 B1
(45) Date of Patent: Mar. 27, 2001

(54) PHARMACEUTICAL COMBINATIONS FOR TREATING OBESITY AND FOOD CRAVING

(76) Inventor: Richard Brian Rothman, 8508 Carlynn Dr, Bethesda, MD (US) 20817

( * ) Notice: Subject to any disclaimer, the term of this patent is extended or adjusted under 35 U.S.C. 154(b) by 0 days.

(21) Appl. No.: 09/335,841

(22) Filed: Jun. 18, 1999

(51) Int. Cl.⁷ ............................ A61K 31/40; A61K 31/31; A61K 31/195
(52) U.S. Cl. ......................... 514/419; 514/416; 514/497; 514/565; 514/567
(58) Field of Search ....................................... 514/419, 416, 514/497, 565, 567

(56) References Cited

PUBLICATIONS

Ceci et al. "The effects of oral 5–hydroxytryptophan administration on feeding behavior in adult female subjects" J.Neural.Transm. 76:109–117, 1989.*

Magnussen et al. "Human pharmacokinetics of long term-hydroxytryptophan combined with decarboxylase inhibitors" Eur. J. Clin. Pharmacolo. 23:81–86, 1982.*

* cited by examiner

Primary Examiner—Jerome D. Goldberg
Assistant Examiner—Jennifer Kim

(57) ABSTRACT

Numerous studies have documented that medications which increase brain serotonin (5-HT) are effective anorectic agents which help obese patients lose weight and which also decrease craving for sweets and carbohydrates. Evidence from other studies also indicate that increases in brain 5-HT may help decrease craving for alcohol and cocaine. 5-hydroxy-L-tryptophan, abbreviated 5-HTP, is the immediate precursor of serotonin (5-HT). When administered in combination with an inhibitor of peripheral decarboxylase such as carbidopa, 5-HTP increases brain serotonin. Increases in synaptic 5-HT decreases the firing rate of 5-HT neurons via stimulation of inhibitory 5-HT1a receptors located on the cell bodies in the raphe. This serves as a negative feedback loop. The clinically available beta adreneric receptor antagonist medication pindolol is also a 5-HT1a antagonist, and can be used to increase the ability of 5-HTP to increase brain 5-HT. Previous studies with 5-HTP used doses exceeding 50 mg per day. When 5-HTP was used in combination with carbidopa, the dose of carbidopa was in excess of 50 mg per day. One novel aspect of the invention are the doses of the 5-HTP and carbidopa: much lower daily doses than have been used before are effective in decreasing appetite, decreasing craving for food and for promoting weight loss. The second novel aspect of the invention relates to the concurrent use of pindolol along with the 5-HTP/Carbidopa, which enhances the effectiveness of the 5-HTP/Carbidopa combination.

4 Claims, No Drawings

PHARMACEUTICAL COMBINATIONS FOR TREATING OBESITY AND FOOD CRAVING

RELATED APPLICATIONS

None.

BACKGROUND OF THE INVENTION

Numerous studies have documented that medications which increase brain 5-HT, such as fenfluramine, are effective anorectic agents which help obese patients lose weight and which also decrease craving for sweets and carbohydrates (6,23). Evidence from other studies also indicate that increases in brain 5-HT may help decrease craving for alcohol and cocaine (1,8,14,15,18–20,24). 5-hydroxy-L-tryptophan, abbreviated 5-HTP, is the immediate precursor of serotonin (5-HT). A goal of treatment with 5-HTP is to increase brain 5-HT. Previous studies in animals and humans have established that administration of 5-HTP increases brain 5-HT (7,13,21). However, 5-HTP administered systemically (intraperitoneal, oral, intravenous) is rapidly converted to 5-HT by an enzyme called peripheral decarboxylase before it ever gets into the brain. Thus, to achieve the desired effect of increasing brain 5-HT it is necessary to co-administer an inhibitor of the enzyme peripheral decarboxylase along with the 5-HTP. A typical means of doing so is to administer carbidopa along with the 5-HTP.

Increases in synaptic 5-HT decreases the firing rate of 5-HT neurons via stimulation of inhibitory 5-HT1a receptors located on the cell bodies in the raphe. This serves as a negative feedback loop. Administration of 5-HT1a receptor antagonists interrupt this feedback loop, and thereby increase the ability of 5-HT reuptake inhibitors to increase synaptic 5-HT (5,9,17). The clinically available beta adreneric receptor antagonist medication pindolol is also a 5-HT1a antagonist, and can be used to increase the ability of 5-HTP to increase brain 5-HT (4,12).

BRIEF SUMMARY OF THE INVENTION

Medications which increase brain serotonin (5-hydroxytryptamine, 5-HT) decrease hunger, craving for food, especially for carbohydrates and candy (i.e. sweets). Evidence from other studies also indicate that increases in brain 5-HT may help decrease craving for alcohol and cocaine (1,8,14,15,18–20,24).

The biosynthesis of 5-HT in the brain proceeds from the uptake of dietary tryptophan by the neuron, followed by its conversion to 5-hydroxytryptophan (abbreviated 5-HTP) by an enzyme called tryptophan hydroxlyase. 5-HTP is decarboxylated to 5-HT by an enzyme called L-aromatic amino acid decarboxylase. When administered to animals or humans, 5-HTP is rapidly decarboxylated by an enzyme called L-amino acid decarboxylase also commonly called peripheral decarboxylase (11). Thus, when administered via the oral, intravenous and other peripheral routes, 5-HTP is rapidly converted to 5-HT and little if any 5-HTP enters the brain. 5-HT itself does not cross the blood brain barrier and any increase in blood 5-HT is removed by uptake into platelets and metabolism by monamine oxidase. Carbidopa is an inhibitor of Laromatic amino acid decarboxylase. Carbidopa does not enter the brain, and thus administration of carbidopa selectively blocks the conversion of 5-HTP to 5-HT in the periphery, but not the brain. Thus, it is well known that co-administration of carbidopa with 5-HTP can be used to increase brain 5-HT (2,10,11). In addition, administration of 5-HT1a receptor antagonists such as pindolol can be used to increase the ability of 5-HTP to increase brain 5-HT (4,12).

The doses of 5-HTP and carbidopa used in various clinical studies were reviewed by Byerley et al. (2) and van Pragg (22). These reviews demonstrate that 5-HTP was used in doses exceeding 50 mg per day and that when 5-HTP was used in combination with carbidopa, the dose of carbidopa was in excess of 50 mg per day. For example, the study by Ceci et al. (3) administered 560 mg of 5-HTP per day.

There are two novel aspects of the invention. One novel aspect of the invention are the doses of the 5-HTP and carbidopa. I have found much lower daily doses than have been used before to be effective in decreasing appetite, decreasing craving for food and for promoting weight loss. In particular, capsules containing [5-HTP (5 mg) plus carbidopa (5 mg)], [5-HTP (10 mg) plus carbidopa (5 mg)] or 5-HTP (15 mg) plus carbidopa (5 mg)] orally administered one to three time per day are particularly effective. The second novel aspect of the invention relates to the concurrent use of pindolol along with the 5-HTP/Carbidopa. In particular, capsules containing [5-HTP (5 mg) plus carbidopa (5 mg) plus pindolol (2 mg)], [5-HTP (10 mg) plus carbidopa (5 mg) plus pindolol (2 mg)] or 5-HTP (15 mg) plus carbidopa (5 mg) plus pindolol (2 mg)] orally administered one to three time per day are particularly effective.

DETAILED DESCRIPTION OF THE INVENTION

The pharmaceutical compounds according to the invention are found in three different classes of therapeutically active substances, i.e. one class comprising the precursor of the neurotransmitter serotonin, such L-5-hydroxytryptophan, the second class comprising inhibitors of the enzyme peripheral decarboxylase, such as carbidopa, and the third class comprising compounds which block the 5-HT1a receptor in the brain, such as pindolol. The term "therapeutically active substance" as used herein is intended to mean any physiologically or pharmacologically active substance that produce a localized or systemic effect in animals, in particular in mammals, including humans, primates and domestic animals.

Examples of peripheral decarboxlyase inhibitors include drugs such as carbidopa and benserazide, or any prodrug which yields a peripheral decarboxylase inhibitor. Examples of 5-HT1a inhibitors include pindolol, but could also include any other drugs blocks activation of 5-HT1a receptor. Examples of 5-HT1a inhibitors also include any prodrug which yields a drug which blocks activation of 5-HT1a receptor.

In this context, the term "prodrug" denotes a bioreversible derivative of the drug, the bioreversible derivative characterized in being therapeutically inactive per se but being able to convert to the active drug within the organism either by an enzymatic or non-enzymatic process.

Pharmaceutically acceptable salts of the compounds according to the present invention include salts of strong inorganic acids or week organic acids, for example a hydrochloride, sulfate, nitrate and acetate salt.

Examples of suitable prodrugs of the compounds according to the present invention include compounds obtained by suitable bioreversible derivatization of one or more reactive groups of the parent drug.

The composition according to the present invention can be formulated for administration by any suitable route such as the oral, rectal, nasal, topical (dermal) or parenteral administration route. Thus, the composition may be in the form of tablets, capsules, suspensions, emulsions, solutions, injectables, suppositories, sprays, aerosols and in other suitable form. Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatin or acacia; and lubricating agents, for example, magnesium stearate, stearic acid or talc. Other pharmaceutically acceptable excipients can be colorants, flavouring agents, plasticizers, humectants etc. The tablets may be uncoated or they may be coated by known techniques, optionally to delay disintegration and absorption in the gastrointestinal tract and thereby provide a sustained action over a longer period. For example, a time delay material such as glyceryl monostearate or glyceryl distearate may be employed. Formulations for oral use may also be presented as chewing tablets, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil. Powders, dispersible powders or granules suitable for preparation of an aqueous suspension by addition of water are also convenient dosage forms of the present invention. Formulation as a suspension provide the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc. The pharmaceutical formulation may also be administered parenterally (intravenous, intramuscular, subcutaneous or the like) in dosage forms or formulations containing conventional, non-toxic pharmaceutically acceptable carriers and adjuvants. The formulation and preparation of such compositions is well-known to those skilled in the art of pharmaceutical formulation. Specific formulation can, however, be found in the text entitled "Remington's Pharmaceutical Sciences" (16).

For parenteral use, the pharmaceutical compositions according to the invention may comprise the therapeutic compounds in the form of a sterile injection. To prepare such a composition, the therapeutic compounds are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl phydroxybenzoate. For the rectal application, suitable dosage forms for a composition according to the present invention include suppositories (emulsion or suspension type), and rectal gelatin capsules (solutions or suspensions). In a typical suppository formulation, the compounds are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives like e.g. enhancers or surfactants may be incorporated. For the nasal application typical dosage forms for a composition according to the present invention include nasal sprays and aerosols for inhalation. In a typically nasal formulation, the active ingredients are dissolved or dispersed in a suitable vehicle. The pharmaceutically acceptable vehicles and excipients and optionally other pharmaceutically acceptable materials present in the composition such as diluents, enhances, flavouring agents, preservatives etc. are all selected in accordance with conventional pharmaceutical practice in a manner understood by the persons skilled in the art of formulating pharmaceuticals.

The pharmaceutical compositions according to the invention may also be administered topically on the skin for percutaneous absorption in dosage forms or formulations containing conventionally non-toxic pharmaceutically acceptable carriers and excipients including microspheres and liposomes. The formulations include creams, ointments, lotions, liniments, gels, hydrogels, solutions, suspensions, pastes, plasters and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes and skin protective agents. Examples of emulsifying agents are naturally occurring gums, e.g. gum acacia or gum tragacanth, naturally occurring phosphatides, e.g. soybean lecithin and sorbitan monooleate derivatives. Examples of antioxidants are butylated hydroxy anisole (BHA), ascorbic acid and derivatives thereof, tocopherol and derivatives thereof and cysteine. Examples of preservatives are parabens and benzalkonium chloride. Examples of humectants are glycerin, propylene glycol, sorbitol and urea. Examples of penetration enhancers are propylene glycol, DMSO, triethanoiamine, N,N-dimethylacetamide, N,N-dimethylformamide, 2-pyrrolidone and derivatives thereof, tetrahydrofurfuryl alcohol and Azone.RTM. Examples of chelating agents are sodium EDTA, citric acid and phosporic acid. Examples of gel forming agents are Carbopol, cellulose derivatives, bentonit, alginates, gelatin and PVP. Examples of ointment bases are beeswax, paraffin, cetyl palmitate, vegetable oil, sorbitan esters of fatty acids (Span), polyethyleneglycols, and condensation products between sorbitan esters of fatty acids and ethylene oxide, e.g. polyoxyethylene sorbitan monooleate (Tween). The formulation and preparation of the above-mentioned compositions is well-known to those skilled in the art of pharmaceutical formulation. Specific formulation can be found in "Remington's Pharmaceutical Sciences" (16).

Preferably, the pharmaceutical composition of the present invention comprises a combination product containing the 5-hydroxytryptophan in combination with the peripheral decarboxylase inhibitor, i.e. in the case of a tablet, one tablet comprises a mixture of the two active components. However, the pharmaceutical composition of the present invention may also be presented in one package comprising two separate containers, one container comprising dosage form of the 5-hydroxytryptophan and the other container comprising a dosage form of the peripheral decarboxylase inhibitor. In such cases, special instructions for substantially concomitant use of the two drugs should be enclosed with the product. The two dosage forms can be the same or they may be different, preferably the two dosage forms are the same.

The pharmaceutical composition of the present invention also comprises a combination product containing the 5-hydroxytryptophan in combination with the peripheral decarboxylase inhibitor and the 5-HT1A receptor antagonist, i.e. in the case of a tablet, one tablet comprises a mixture of the three active components. However, the pharmaceutical composition of the present invention may also be presented in one package comprising three separate containers, one container comprising dosage form of the 5-hydroxytryptophan, the second container comprising a dosage form of the peripheral decarboxylase inhibitor and the third container comprising a dosage form of the 5-HT1A receptor antagonist. In such cases, special instructions for substantially concomitant use of the three drugs should be enclosed with the product. The three dosage forms can be the same or they may be different, preferably the three dosage forms are the same.

In one aspect the present invention relates to a method for treatment of overweight or obesity in individuals, in particular in humans, or for reducing the adipose tissue mass/lean mass body mass ratio of an individual, in particular a human.

In the present context the term "overweight" is used as an indication of a body with a weight exceeding the "desirable weight", whereas the term "obesity" is used when the body weight is 20% or more above the "desirable weight". Desirable weights for humans are defined as a body mass index less than or equal to 24.

In another aspect, the present invention relates to a method for the treatment of diseases which are complications to overweight or obesity. These diseases or conditions include diabetes mellitus type II, hypercholesterolemia, hypertriglyceridaemia, hypertension, back pain caused by obesity, arthritis made worse by obesity, sleep apnea and psychological or psychiatric problems complicated by obesity.

In another aspect, the present invention also relates to a method of reducing craving, or the desire to eat foods, consume alcohol or use stimulant drugs such as cocaine or amphetamine-type drugs.

In a further aspect, the invention can be used along with other appetite suppressant drugs, such as amphetamine, phentermine, diethylpropion, phendimetrazine, ephedrine or similarly-acting agents, to enhance the effects of these medications, that is to increase the weight loss which would occur with the use of these agents alone.

In a further aspect, the present invention also relates to the use of a combination of 5-hydroxytryptophan and a peripheral decarboxylase inhibitor for the manufacture of a pharmaceutical composition for the treatment of overweight or obesity or diseases aggravated thereof.

Evidence for Utility

Study 1. 5-HTP/Carbidopa/Pindolol enhances the weight-loss effect of phentermine.

The weight loss experienced over the first month of treatment of patients treated with phentermine (n=29) was compared to patients treated with phentermine plus 5-HTP/Carbidopa/Pindolol (n=37). The patients were matched for starting weight. The average daily weight loss for the phentermine only group was 0.37±0.03 pounds/per day vs. 0.57±0.05 (mean±sem) for the phentermine plus 5-HTP/Carbidopa/Pindolol group.

Study 2. Administration of 5-hydroxytryptophan (5 mg)/Carbidopa (5 mg) decreases craving for food and "sweets".

Patients (n=3) were administered in a single blind manner placebo capsules three times a day for 1 week. In the next week, patients were administered identical capsules three times a day containing 5-hydroxytryptophan (5 mg)/Carbidopa (5 mg).

Patients' craving for food or sweets was rated before treatment, after one week of placebo treatment and after one week of treatment with 5-hydroxytryptophan (5 mg)/Carbidopa (5 mg). The rating scale ranged from 1 for no Craving to 10 for the most craving ever. The results demonstrated that placebo treatment reduced craving by 14±7% (mean+SEM, n=3) and 5-hydroxytryptophan (5 mg)/Carbidopa (5 mg) reduced craving by 82±3 (mean±SEM, n=3). Patients also reported the degree to which intake of foods they craved were reduced. In this questionnaire 1=much reduced, 2=a little reduced, 3=no change and 4=increased. The results were as follows: week 1 2.5+0.5 (mean±SEM, n=3) indicating little reduction by placebo. At the end of week 2 intake was rated as 1±0 (mean±SEM, n=3), indicating a large reduction in the intake of craved foods.

REFERENCES

1. Brauer, L. H.; Johanson, C. E.; Schuster, C. R.; Rothman, R. B.; de Wit, H. Evaluation of phentermine and fenfluramine, alone and in combination, in normal, healthy volunteers. Neuropsychopharmacol. 14:233–241; 1996.
2. Byerley, W. F.; Judd, L. L.; Reimherr, F. W.; Grosser, B. I. 5-Hydroxytryptophan: a review of its antidepressant efficacy and adverse effects. J.Clin.Psychopharmacol. 7:127–137; 1987.
3. Ceci, F.; Cangiano, C.; Cairella, M.; Cascino, A.; Del Ben, M.; Muscaritoli, M.; Siblilia, L.; Fanelli, F. R. The effects of oral 5-hydroxytryptophan administration on feeding behavior in adult female subjects. J.Neural.Transm. 76:109–117; 1989.
4. Dawson, L. A.; Nguyen, H. Q. Effects of 5-Ht1A Receptor Antagonists on Fluoxetine-Induced Changes in Extracellular Serotonin Concentrations in Rat Frontal-Cortex. Eur.J.Pharmacol. 345:41–46; 1998.
5. Dreshfield, L. J.; Wong, D. T.; Perry, K. W.; Engleman, E. A. Enhancement of fluoxetine-dependent increase of extracellular serotonin (5-HT) levels by (-)-pindolol, an antagonist at 5-HT1A receptors. Neurochem.Res. 21:557–562; 1996.
6. Garattini, S.; Mennini, T.; Samanin, R. Reduction of food intake by manipulation of central serotonin. Current experimental results. Br.J.Psychiatry Suppl. 41–51; 1989.
7. Gartside, S. E.; Cowen, P. J.; Sharp, T. Effect of 5-hydroxy-L-tryptophan on the release of 5-HT in rat hypothalamus in vivo as measured by microdialysis. Neuropharmacology. 31:9–14; 1992.
8. Hitzig, P. Combined serotonin and dopamine indirect agonists correct alcohol craving and alcohol-associated neurosis. J.Subst.Abuse.Treat. 11:489–490; 1994.
9. Hjorth, S. (-)-Pindolol, but not buspirone, potentiates the citalopram-induced rise in extracellular 5-hydroxytryptamine. Eur.J.Pharmacol. 303:183–186; 1996.
10. Magnussen, I. Effects of carbidopa on the cerebral accumulation of exogenous L-5-hydroxytryptophan in mice. Acta Pharmacol.Toxicol.(Copenh). 55:199–202; 1984.
11. Magnussen, I.; Van Woert, M. H. Human pharmacokinetics of long term 5-hydroxytryptophan combined with decarboxylase inhibitors. Eur.J.Clin.Pharmacol. 23:81–86; 1982.
12. Meltzer, H. Y.; Maes, M. Effect of pindolol on the L-5-HTP-induced increase in plasma prolactin and cortisol concentrations in man. Psychopharmacol 114:635–643; 1994.
13. Meltzer, H. Y.; Maes, M. Effect of pindolol on the L-5-HTP-induced increase in plasma prolactin and cortisol concentrations in man. Psychopharmacol 114:635–643; 1994.
14. Mirovsky, Y.; Yu, Y.-L.; Wagner, G. C.; Sekowski, A.; Goldberg, M.; Fisher, H. Novel synergistic treatment of ethanol withdrawal seizures in rats with dopamine and serotonin agonists. Alcohol.Clin.Exp.Res. 19:160–163; 1995.
15. Rea, W. P.; Rothman, R. B.; Shippenberg, T. S. Evaluation of the conditioned reinforcing effects of phentermine and fenfluramine in the rat: concordance with clinical studies. Synapse 30:107–111; 1998.
16. Remington, J. P. *Remington's Pharmaceutical Sciences,* Easton, Pa.:Mack Publishing Company, 1980. Ed. 16.
17. Romero, L.; Bel, N.; Artigas, F.; de Montigny, C.; Blier, P. Effect of pindolol on the function of pre- and postsynaptic 5-HT1A receptors: in vivo microdialysis and electrophysiological studies in the rat brain [published erratum appears in Neuropsychopharmacology 1997 Jan;16 (1):91]. Neuropsychopharmacology. 15:349–360; 1996.
18. Rothman, R. B. Treatment of alcohol and cocaine addiction by the combination of pemoline and fenfluramine: a preliminary case series. J.Subst.Abuse.Treat. 12:449–453; 1995.
19. Rothman, R. B.; Elmer, G. I.; Shippenberg, T. S.; Rea, W.; Baumann, M. H. Phentermine and fenfluramine: preclinical studies in animal models of cocaine addiction. Annals of the New York Academy of Sciences 844:59–74; 1998.
20. Rothman, R. B.; Gendron, T. M.; Hitzig, P. Combined use of fenfluramine and phenternine in the treatment of cocaine addiction: a pilot case series. J.Subst.Abuse.Treat. 11:273–275; 1994.
21. Shimizu, N.; Take, S.; Hori, T.; Oomura, Y. In vivo measurement of hypothalamic serotonin release by intracerebral microdialysis: significant enhancement by immobilization stress in rats. Brain Research Bulletin 28:727–734; 1992.
22. van Praag, H. M. Serotonin precursors in the treatment of depression. Adv.Biochem.Psychopharmacol. 34:259–286; 1982.
23. Wurtman, R. J.; Wurtman, J. J. Brain serotonin, carbohydrate-craving, obesity and depression. Obes.Res. 3 Suppl 4:477S–480S; 1995.
24. Yu, Y. L.; Fisher, H.; Sekowski, A.; Wagner, G. C. Amphetamine and fenfluramine suppress ethanol intake in ethanol-dependent rats. Alcohol. 14:45–48; 1997.

What is claimed is:

1. A method for reducing the weight of a human, comprising administering to the human in need thereof a synergistic combination with effective amounts of 1–15 mg of L-5-hydroxytryptophan, 1–8 mg of carbidopa, and 1–5 mg of pindolol.

2. A method in claim 1, said synergistic combination with effective amounts, is 15 mg of L-5-hydroxytryptophan, 5 mg of carbidopa, and 2 mg of pindolol.

3. A method in claim 1, said synergistic combination with effective amounts, is 10 mg of L-5-hydroxytryptophan, 5 mg of carbidopa, and 2 mg of pindolol.

4. A method in any one of claims 1, 2, or 3 may be also be administered in combination with an effective amount of other anorectic agents selected from group consisting of phentermine, diethylpropion, phendimetrazine and ephedrine.

\* \* \* \* \*